(12) United States Patent
Gross

(10) Patent No.: US 6,932,808 B2
(45) Date of Patent: Aug. 23, 2005

(54) ABLATION SHAPE FOR THE CORRECTION OF PRESBYOPIA

(75) Inventor: Erik Gross, Palo Alto, CA (US)

(73) Assignee: Visx, Incorporated, Santa Clara, CA (US)

( * ) Notice: Subject to any disclaimer, the term of this patent is extended or adjusted under 35 U.S.C. 154(b) by 199 days.

(21) Appl. No.: 10/300,721

(22) Filed: Nov. 19, 2002

(65) Prior Publication Data

US 2004/0097909 A1 May 20, 2004

(51) Int. Cl.[7] .................................. A61F 9/007
(52) U.S. Cl. ..................... 606/10; 606/5; 606/13
(58) Field of Search .................. 606/3, 5, 10–14, 606/17, 18

(56) References Cited

U.S. PATENT DOCUMENTS

| | | | |
|---|---|---|---|
| 4,665,913 A | 5/1987 | L'Esperance, Jr. | |
| 4,669,466 A | 6/1987 | L'Esperance | |
| 4,732,148 A | 3/1988 | L'Esperance | |

(Continued)

FOREIGN PATENT DOCUMENTS

WO    WO 02/085231 A1    10/2002

OTHER PUBLICATIONS

Loewenfeld, Irene, E., *The Pupil: Anatomy, Physiology and Clinical Applications*, vol. 1, (© 1993) Wayne State University Press, Detroit, MI, pp. 296, 301–304.

Morelra et al., "Multifocal Corneal Topographic Changes with Excimer Laser Photorefractive Keratectomy" *Arch. Ophthalmol.* (1992) 110: 994–999.

Vinciguerra et al., "Excimer Laser Photorefractive Keratectomy for Presbyopia: 24–month Follow–up in Three Eyes" *Journal of Refractive Surgery* (198) 14:31–31.

Anschutz, T. (1994). "Laser correction of hyperopia and presbyopia," *Int. Ophthalmol Clin.* 34(4):107–137.

Josephson, J.E. (1993). "Corneal Bifocal Effects by Laser Photorefractive Keratectomy," *Arch Ophthalmol*vol. 111, pp. 582.

*Primary Examiner*—David M. Shay
(74) *Attorney, Agent, or Firm*—Townsend & Townsend & Crew LLP; Mark D. Barrish, Esq.

(57) ABSTRACT

Improved refractive eye surgery methods, apparatus and systems employ ablative photodecomposition of a cornea to mitigate and/or inhibit presbyopia with minimal vision degradation. A method for treating a cornea includes ablating a superior area of the cornea to enhance near-distance vision and ablating an inferior area of the cornea to enhance far-distance vision. Typically, the inferior area corresponds to an area of the cornea that is blocked (generally by the lower eyelid and/or cheek) from viewing objects when the eye is facing downward. The superior area corresponds to an area of the cornea that is blocked from viewing objects (generally by the patient's upper eyelid) when the eye is facing forward or slightly above the horizon. In some embodiments, a transition zone is ablated between the superior and inferior areas, to enable a smoother visual transition between the two areas.

17 Claims, 4 Drawing Sheets

U.S. PATENT DOCUMENTS

| | | |
|---|---|---|
| 4,770,172 A | 9/1988 | L'Esperance, Jr. |
| 4,773,414 A | 9/1988 | L'Esperance, Jr. |
| 5,163,934 A | 11/1992 | Munnerlyn |
| 5,314,422 A | 5/1994 | Nizzola |
| 5,395,356 A | 3/1995 | King et al. |
| 5,485,228 A | 1/1996 | Roffman et al. |
| 5,533,997 A | 7/1996 | Ruiz |
| 5,556,395 A | 9/1996 | Shimmick et al. |
| 5,682,223 A | 10/1997 | Menezes et al. |
| 5,683,379 A | 11/1997 | Hohla |
| 5,684,560 A | 11/1997 | Roffman et al. |
| 5,724,258 A | 3/1998 | Roffman |
| 5,803,923 A | 9/1998 | Singh-Derewa et al. |
| 5,807,377 A | 9/1998 | Madhani et al. |
| 5,827,264 A | 10/1998 | Hohla |
| 5,835,192 A | 11/1998 | Roffman et al. |
| 5,864,379 A | 1/1999 | Dunn |
| 6,106,513 A * | 8/2000 | McMillen et al. .............. 606/5 |
| 6,162,210 A | 12/2000 | Shadduck |
| 6,200,342 B1 | 3/2001 | Tassignon |
| 6,245,059 B1 | 6/2001 | Clapham |
| 6,258,082 B1 | 7/2001 | Lin |
| 6,280,435 B1 | 8/2001 | Odrich et al. |
| 6,312,424 B1 * | 11/2001 | Largent .......................... 606/5 |
| 6,554,429 B1 | 4/2003 | Campin et al. |
| 6,679,606 B2 | 1/2004 | Campin et al. |
| 6,682,196 B2 | 1/2004 | Sheets, Jr. et al. |
| 2002/0140902 A1 | 10/2002 | Guirao et al. |
| 2003/0199858 A1 | 10/2003 | Schelonka |

* cited by examiner

ABLATION SHAPE FOR THE CORRECTION OF PRESBYOPIA

BACKGROUND OF THE INVENTION

Field of the Invention

This invention relates to surgical modifications to the eye. In a specific embodiment, the invention provides ophthalmic surgery techniques which employ a laser to effect ablative photodecomposition of corneal tissue to correct presbyopia and/or other vision defects.

With aging, a condition of the eye known as presbyopia develops. With this condition, the crystalline lens of the eye loses the ability to focus on near objects when the eye is corrected for far-vision.

Presbyopia is often treated with bifocal eyeglasses. With bifocals, one portion of the lens is corrected for far-vision, and another portion of the lens is corrected for near-vision. By looking down through the bifocals, the user looks through the portion of the lens corrected for near-vision. When viewing distant objects, the user looks higher, through the portion of the bifocals corrected for far-vision.

Efforts have been made to treat presbyopia using partitioned lenses positioned directly over the pupil of the eye. Examples include multifocal contact lenses. Unfortunately, when presbyopia is corrected with bifocal or multifocal lenses attached to the cornea, the user is simultaneously looking through the near- and far-vision corrected lenses. As a result, the user may see both in-focus and out-of-focus images simultaneously when viewing an object. This out-of-focus image superimposed on the in-focus image may cause glare and degrade vision, particularly when viewing objects at low contrast.

Another technique for treating presbyopia has been to correct one eye of the patient for near-vision and to correct the other eye for distance-vision. This technique is known as monovision. With monovision, a patient uses one eye to see distant objects and the other eye to see close objects. While generally effective, monovision may not allow the patient to clearly see objects that are intermediately positioned, and seeing with only one eye may be disadvantageous for some patients.

Laser-based systems and methods are known for enabling ophthalmic surgery on the cornea in order to correct vision defects by the technique known as ablative photodecomposition. Changing the shape of the anterior surface of the cornea will change the optical properties of an eye. These ablative photodecomposition systems and methods control ultraviolet laser radiation flux density and exposure time upon the cornea so as to achieve a desired surface change in the cornea and thereby correct an optical defect.

In a typical laser surgical procedure, the optically functional region of the corneal surface to be ablated is designated the optical zone. Depending on the nature of the desired optical correction, the optical zone may or may not be centered on the center of the pupil or on the apex of the corneal surface.

Several different ablative photodecomposition techniques have been described to correct specific optical errors of the eye. For example, a myopic condition may be corrected by laser sculpting a corneal surface to reduce curvature. An astigmatic condition, which is typically characterized by a cylindrical component of curvature (departing from the otherwise generally spherical curvature of the cornea), can be corrected by a cylindrical ablation. Laser sculpting a corneal surface to increase the curvature can correct a hyperopic condition.

Efforts have also been made to treat presbyopia using ablative photodecomposition. One specific technique of treating presbyopia creates near-vision correction by ablating a region of the lower portion of the cornea adjacent the pupil rim. Alternative suggested presbyopia treatments include laser ablation of an annular region of the cornea, or the ablation of a central lens for near-vision, surrounded by a gradual blend zone, and then a peripheral far-vision lens, all within the optically used portion of the cornea.

In many of these previously proposed approaches, a treated patient will often look through a portion of the cornea treated for near-distance when trying to focus on far-distance objects, and will also look through a portion of the cornea treated for far-distance even when trying to focus on near-distance objects. For example, in monocular treatments, where one eye is treated for near vision and the other is treated for far vision, a patient looks through both the near-vision eye and the far-vision eye, regardless of whether the patient is trying to view near or far objects. When different areas of each eye are treated for different vision, a patient may actually look through an area treated for one type of vision when trying to view an object at another distance. This may cause complaints and lead to less than ideal visual acuity.

Therefore, new photoablative methods, devices and systems are needed, to provide improved treatment of presbyopia.

DESCRIPTION OF THE BACKGROUND ART

Systems and methods relevant to laser-based treatments for presbyopia are disclosed in the following U.S. patents and patent applications, the entire disclosures of which are hereby incorporated by reference: U.S. Pat. No. 5,314,422, issued May 24, 1994, for "Equipment for the Correction of Presbyopia by Remodeling the Corneal Surface by Means of Photoablation"; U.S. Pat. No. 5,395,356, issued Mar. 7, 1995, for "Correction of Presbyopia by Photorefractive Keratectomy"; U.S. Pat. No. 5,533,997, issued Jul. 9, 1996, "Apparatus and Method for Performing Presbyopia Correction"; U.S. Pat. No. 5,803,923, issued Sep. 8, 1998, for "Presbyopia Correction Using a Protected Space Pattern, Methods and Apparatus"; U.S. Pat. No. 6,162,210, issued Dec. 19, 2000, for "Laser Mediated Treatments for Presbyopia and Hyperopia"; U.S. Pat. No. 6,258,082, issued Jul. 10, 2001, for "Refractive Surgery and Presbyopia Correction Using Infrared and Ultraviolet Lasers"; and U.S. Pat. No. 6,280,435, issued Aug. 28, 2001, for "Method and Systems for Laser Treatment of Presbyopia Using Offset Imaging."

Ablative photodecomposition systems and methods are disclosed in the following U.S. patents and patent applications, the entire disclosures of which are hereby incorporated by reference: U.S. Pat. No. 4,665,913, issued May 19, 1987, for "Method for Ophthalmical Surgery"; U.S. Pat. No. 4,669,466, issued Jun. 2, 1987, for "Method and Apparatus for Analysis and Correction of Abnormal Refractive Errors of the Eye"; U.S. Pat. No. 4,732,148, issued Mar. 22, 1988, for "Method for Performing Ophthalmic Laser Surgery"; U.S. Pat. No. 4,770,172, issued Sep. 13, 1988, for "Method of Laser Sculpture of the Optically Used Portion of the Cornea"; U.S. Pat. No. 4,773,414, issued Sep. 27, 1988, for "Method of Laser Sculpture of the Optically Used Portion of the Cornea"; U.S. patent application Ser. No. 07/109,812, filed Oct. 16, 1987, for "Laser Surgery Method and Apparatus"; U.S. Pat. No. 5,163,934, issued Nov. 17, 1992, for "Photorefractive Keratectomy"; U.S. Pat. No. 5,556,395, issued Sep. 17, 1996, for "Method and System for Laser Treatment of Refractive Error Using an Offset Image of a Rotatable Mask"; U.S. patent application Ser. No. 08/368,799, filed Jan. 4, 1995, for "Method and Apparatus for Temporal and Spatial Beam Integration"; U.S. patent application Ser. No. 08/058,599, filed May 7, 1993, for "Method and System for Laser Treatment of Refractive Errors Using Offset Imaging"; U.S. Pat. No. 5,683,379, issued Nov. 4, 1997, for "Apparatus for Modifying the Surface of the Eye Through Large Beam Laser Polishing and Method of Controlling the Apparatus"; U.S. Pat. No. 5,827,264, issued Oct. 27, 1998 for "Method of Controlling Apparatus for Modifying the Surface of the Eye Through Large Beam Laser Polishing"; and U.S. Pat. No. 6,245,059, issued Jun. 12, 2001, for "Offset Ablation Profiles for Treatment of Irregular Astigmatism."

Techniques for treating presbyopia with contact lenses are disclosed in the following U.S. patents and patent applications, the entire disclosures of which are hereby incorporated by reference: U.S. Pat. No. 5,835,192, issued Nov. 10, 1998, for "Contact Lens and Method of Fitting a Contact Lens"; U.S. Pat. No. 5,485,228 issued Jan. 16, 1996 for "Multifocal Ophthalmic Lens Pair;" and U.S. Pat. No. 5,864,379 issued Jan. 26, 1999 for "Contact Lens and Process for Fitting."

BRIEF SUMMARY OF THE INVENTION

The present invention generally provides improved refractive eye surgery methods, apparatus and systems to mitigate and/or inhibit presbyopia with minimal vision degradation. A method is provided for ablating a superior area and an inferior area of a cornea. In some embodiments, the superior area is ablated to improve its near-vision capabilities and the inferior area is ablated to improve its far-vision capabilities. Typically, the inferior area is blocked (generally by the patient's lower eyelid and/or cheek) from viewing objects when the eye is facing downward. The superior area is blocked from viewing objects (generally by the patient's upper eyelid) when the eye is facing forward or slightly above the horizon. Thus, a patient will typically view near objects through the superior area of the cornea, which is ablated to improve near vision, and will typically view far objects through the inferior area of the cornea, which is ablated to improve far vision.

In some embodiments, a transition zone will be ablated between the superior and inferior areas, to enable a smoother vision transition between the superior and inferior areas. The superior area, inferior area and transition zone may generally define an optical zone, in certain embodiments. Typically, the invention also provides for scaling the optical zone to match the size of a pupil of a patient.

By providing improved methods, apparatus and systems for photoablative presbyopia treatment, the present invention enables a patient to have improved vision of both near and far objects without the disadvantages of currently available alternative treatments, such as bifocals, monocular surgery and the like. With the present invention, patients will be able to use both eyes to view either a far or a near object and will not have to view objects simultaneously through differently-corrected portions of lenses, contacts, corneas and the like, as typically occurs with bifocals and similar devices and treatments.

In one aspect, the present invention provides a method for treating a cornea of an eye to correct presbyopia, the cornea having a superior area toward the top of a patient's head and an inferior area toward the patient's feet. The method includes ablating the superior area of the cornea to provide a near-distance vision upper refractive shape and ablating the inferior area of the cornea to provide a far-distance vision lower refractive shape. Optionally, the superior area is ablated to achieve a refraction of about −1 diopter and the inferior area is ablated to achieve a refraction of about 0 diopters.

In some embodiments, the method also includes ablating a transition area of the cornea, the transition area being disposed between the superior area and the inferior area. The transition area, for example, may be ablated to achieve a refraction of about −0.75 diopters in an area adjacent the superior area, a refraction of about −0.25 diopters in an area adjacent the inferior area, and a refraction of about −0.50 diopters in an area approximately midway between the superior area and the inferior area. In various embodiments, the inferior area and the transition area define an optical zone, which may optionally have a diameter of about 4–8 mm.

Generally, the superior area is configured such that vision from the superior area is predominantly blocked by one or more parts of a patient's body (such as an upper eyelid) when the eye focuses straight forward towards the horizon. The inferior area is configured such that vision from the inferior area is predominantly blocked by one or more other parts of a patient's body (such as a lower eyelid and/or cheek) when the eye focuses in a downward direction.

In another aspect, the present invention provides a method for reprofiling a cornea of an eye from an initial shape to a multifocal aspheric shape for correcting presbyopia, the cornea having a superior area toward the top of a patient's head and an inferior area toward the patient's feet. The method includes first aligning a laser system with the eye, the laser system being operable to deliver ablative radiation to the cornea. Next, the cornea is ablated to an ablated shape by selectively exposing the cornea to the ablative radiation so that an optical zone extends across the pupil, the optical zone comprising the superior area ablated to achieve a refraction of about −1 diopter and the inferior area ablated to achieve a refraction of about 0 diopters. Finally, the method includes covering the ablated surface to produce a final aspheric corneal surface.

Optionally, the optical zone further comprises a transition area. In some embodiments, the transition area is ablated to achieve a refraction of about −0.75 diopters in an area adjacent the superior area, a refraction of about −0.25 diopters in an area adjacent the inferior area, and a refraction of about −0.50 diopters in an area approximately midway between the superior area and the inferior area. The transition zone may gradually vary between the superior and inferior areas.

In yet another aspect, the present invention provides a system for treating presbyopia. The system comprises a laser system being operable to deliver ablative radiation to a cornea, the laser system including a processor for processing at least one machine readable code, and a tangible medium removably couplable with the processor. Generally, the tangible medium includes the machine readable code and the machine readable code includes instructions for the laser system to ablate a superior area of the cornea and an inferior area of the cornea.

In many embodiments, the superior area is disposed toward the top of the patient's head and is configured such that vision from the superior area is predominantly blocked by one or more parts of the patient's body when the eye focuses straight forward towards the horizon. Similarly, the inferior area is disposed toward the patient's feet and is configured such that vision from the inferior area is predominantly blocked by one or more other parts of the patient's body when the eye focuses in a downward direction. In some embodiments, the machine readable code further includes instructions for the laser system to ablate the superior area to provide a near-distance vision upper refractive shape and to ablate the inferior area of the cornea to provide a far-distance vision lower refractive shape. Optionally, the machine readable code further includes instructions for the laser system to ablate a transition area of the cornea, the transition area being disposed between the superior area and the inferior area.

In yet another aspect, the present invention provides an apparatus for treating presbyopia. The apparatus generally includes a tangible medium which has at least one machine readable code. The machine readable code includes instructions for a laser system to ablate a superior area and an inferior area of a cornea of a patient.

DETAILED DESCRIPTION OF THE INVENTION

The present invention generally provides improved refractive eye surgery methods, apparatus and systems to mitigate and/or inhibit presbyopia with minimal vision degradation. While the present invention will often be described with reference to the mitigation of presbyopia in combination with refractive hyperopia and/or myopia treatment, the benefits of the present invention are not limited to these specific procedures. Presbyopia treatment techniques of various embodiments of the present invention may be used when no other refractive correction (other than the correction, mitigation, and/or inhibition of presbyopia) is desired. Alternatively, embodiments of the present invention may be combined with therapies for one or more of astigmatism, irregular refractive aberrations, and the like, as well as with hyperopia and/or myopia. Still other aspects of the present invention, including methods and systems which accommodate and adjust for re-epithelization, may find uses in a broad variety of ophthalmologic procedures.

Figure 1:
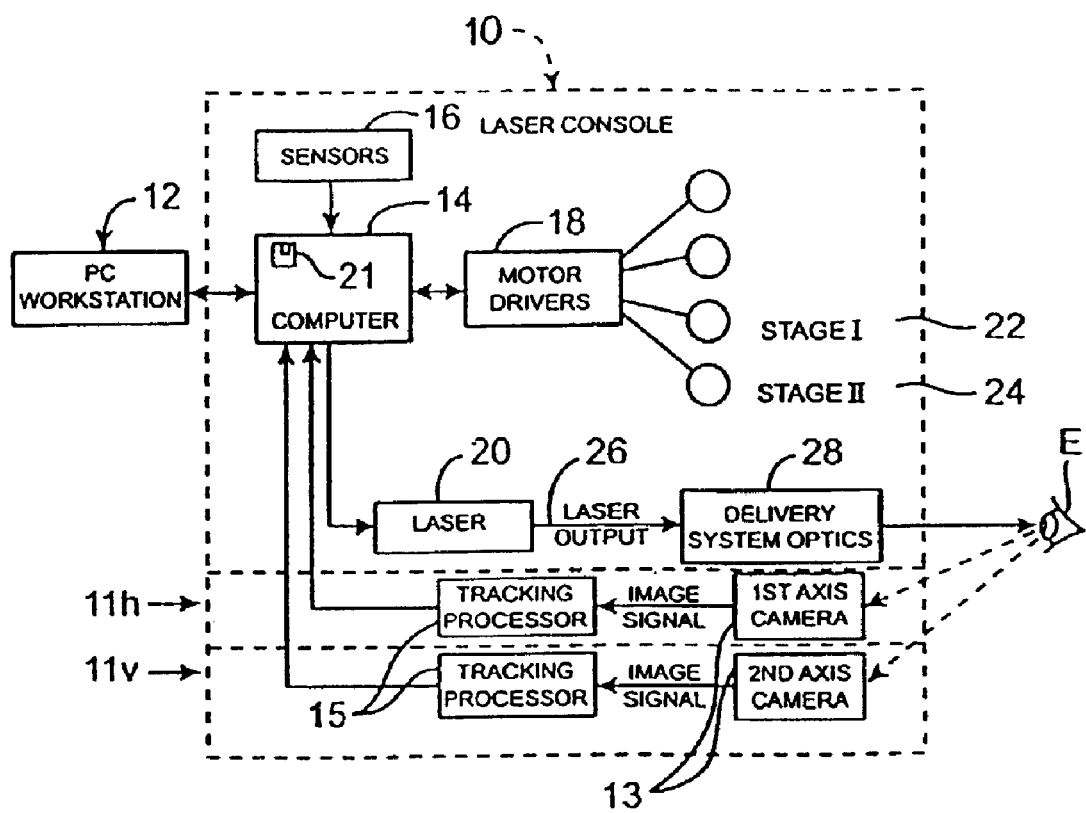
FIG. 1 is a diagram illustrating a laser eye surgery system for ablating a cornea according to one embodiment of the present invention.

Referring now to FIG. 1, a laser surgery system 10 as in various embodiments of the present invention is similar to that described in U.S. Pat. No. 6,322,216, issued Nov. 27, 2001, entitled Two Camera Off-Axis Eye Tracker for Laser Eye Surgery, the entire contents of which is incorporated herein by reference. Generally, laser surgery system 10 has horizontal and vertical trackers 11$h$, 11$v$. Each of trackers 11 includes a camera 13 and an associated tracking processor 15. Where differentiated in the following description, these components may be referred to as horizontal camera 13$h$, vertical camera 13$v$, and the like.

Laser surgery system 10 also includes a laser 20 which generates a laser beam 26 that is selectively directed toward eye E by delivery system optics 28. Delivery system optics 28 scan beam 26 over the corneal tissue of eye E according to instructions from computer 14. Computer 14 generally scans beam 26 over eye E by changing the angular position of first and second stage pivot systems 22, 24 (described below). In alternative embodiments, computer 14 may scan the beam by pivoting one or more mirrors using galvanometric motors, or any of a wide variety of alternative scanning mechanisms. Optionally, computer 14 may direct profiling of beam 26 using one or more variable apertures.

As also shown in FIG. 1, laser surgery system 10 includes a personal computer workstation 12 coupled to computer 14. Laser surgery system 10 may include a plurality of sensors (generally designated by reference no. 16) which produce feedback signals from moveable mechanical and optical components, such as those described in European Patent Application Publication No. 628298, the entire contents of which is hereby incorporated by reference. PC workstation 12 and computer 14 may be combined in a single processor structure, or processing functions may be distributed in a wide variety of alternative arrangements. Similarly, tracking processor modules 15 may comprise one or more separate processing structures from computer 14, or may be integrated into computer 14 as a single processor or with a wide variety of distributed processing arrangements. Computer 14 may comprise a tangible medium 21 embodying the methods of the present invention in a machine readable code. Suitable tangible media include floppy disks, compact optical disks (CDs), removable hard disks, and/or the like. In other embodiments, code may be downloaded from a communication modality such as the Internet, stored as hardware, firmware, software, or the like.

In response to signals provided by tracking processor modules 15 and sensors 16, and according to the sculpting to be performed on the eye to alleviate an optical defect, computer 14 transmits command signals to motor drivers 18 and to laser 20. In response to these command signals, motor drivers produce signals to change an angular orientation of first stage pivot system 22 and second stage pivot system 24, and to operate the other components of the laser delivery system, such as to vary a size of a variable diameter iris to correct myopia, to control the distance between a pair of parallel blades so as to vary a width of the laser beam, to rotate an angular orientation of the parallel blades and rectangular beam to correct astigmatism, and the like. Computer 14 can compensate for lateral movement of the eye during a sculpting procedure by directing the motor driver to reposition the beam (typically by movement of the first and second stages 22, 24) so that the therapeutic pattern of laser energy which is to be directed at the eye remains aligned with the eye during voluntary and/or involuntary movements of the eye.

Laser 20 may include, but is not limited to, an excimer laser such as an argon-fluoride excimer laser producing laser energy with a wavelength of about 193 nm. Alternative laser systems may include solid state lasers, such as frequency multiplied solid state lasers, flashlamp and diode pumped solid state lasers, and the like. Exemplary solid state lasers include UV solid state lasers producing wavelengths of approximately 188–240 nm such as those disclosed in U.S. patent Ser. Nos. 5,144,630, and 5,742,626; and in Borsuztky et al., *Tunable UV Radiation at Short Wavelengths (188–240* nm) *Generated by Frequency Mixing in Lithium Borate*, Appl. Phys. 61:529–532 (1995). A variety of alternative lasers might also be used. The laser energy will generally comprise a beam formed as a series of discreet laser pulses, and the pulses may be separated into a plurality of beamlets.

Figure 2A:
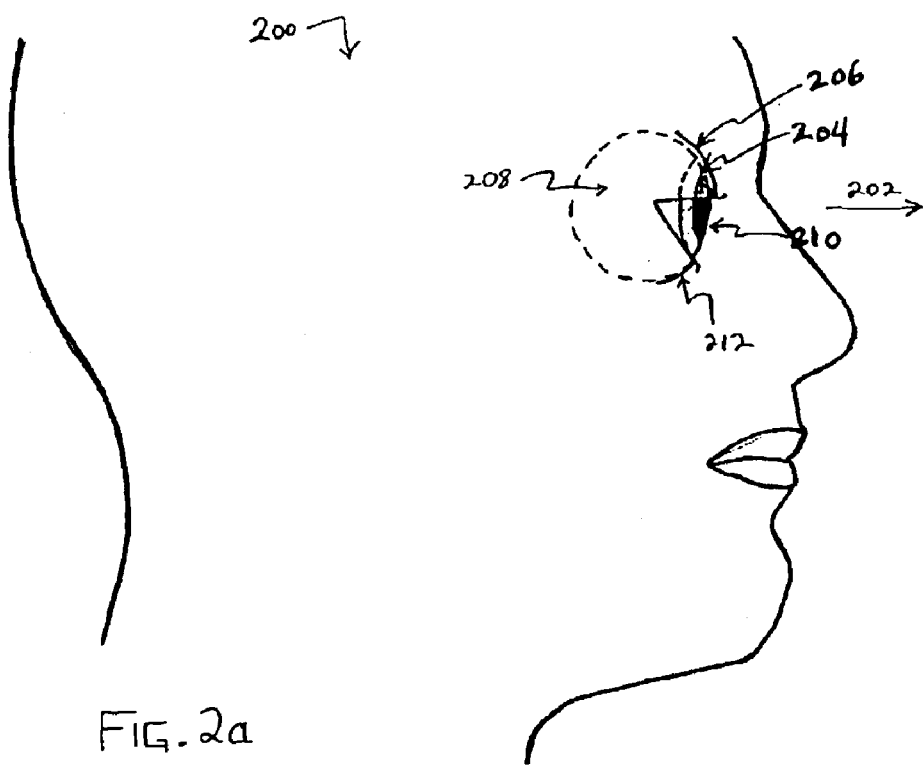
FIG. 2a is a side-view illustration of a human looking in a horizontal direction, for example as in viewing an object that is far away, toward the horizon.

Referring now to FIG. 2a, when a person 200 looks in a forward, or horizontal, direction, as designated by arrow 202, a superior area 204 of the cornea is typically blocked from use by the upper eyelid 206. (Portion of eye 208 residing behind skin, bone, muscle and/or other structures is depicted by dotted line.) Inferior area 210, which is not blocked by the lower eyelid 212, is typically used for viewing one or more objects in a forward/horizontal location. In general, then, inferior area 210 is predominantly used for viewing far objects, which are generally found in a forward/horizontal location in relation to person 200. If person 200 were viewing far-distance objects located laterally from person 200, a similar superior area 204 of the cornea would be blocked and a similar inferior area 210 of the cornea would be used for viewing the objects.

Figure 2B:
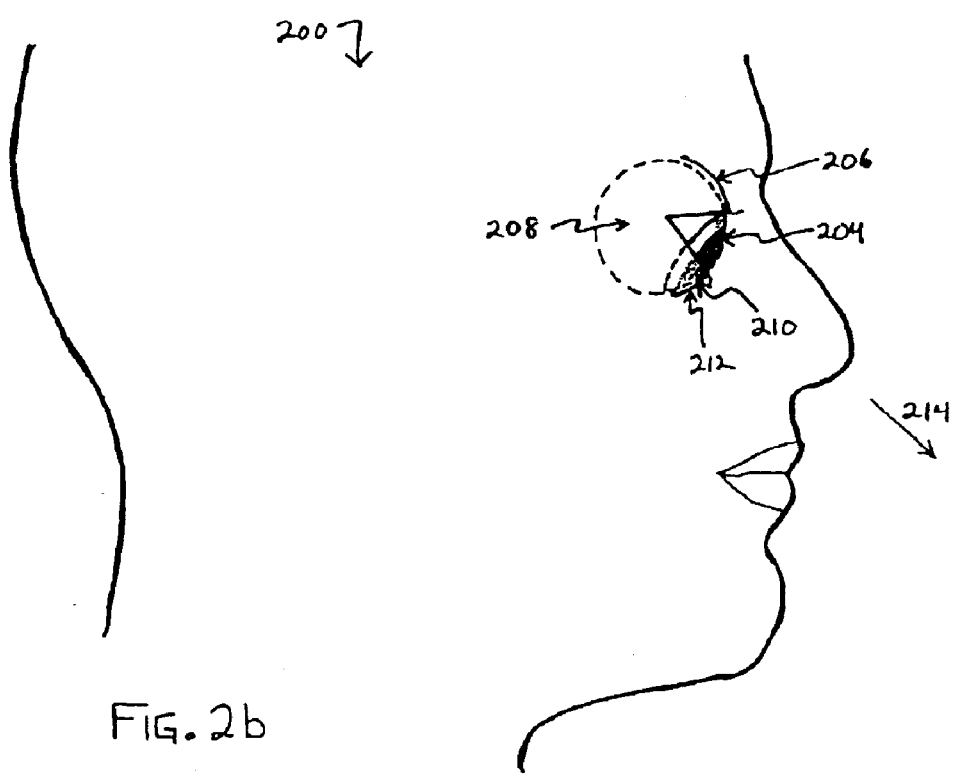
FIG. 2b is a side-view illustration of a human looking in a downward direction, for example as in reading a book.

Referring now to FIG. 2b, when person 200 looks in a downward direction, as designated by arrow 214, inferior area 210 is blocked from use by lower eyelid 212 and/or the person's cheek (not shown) and superior area 204 is able to be used for viewing objects. Typically, person 200 will look in a downward direction to view near objects, such as a book, an object on a table, and the like. Thus, superior area 204 is predominantly used for viewing near objects.

Figure 3:
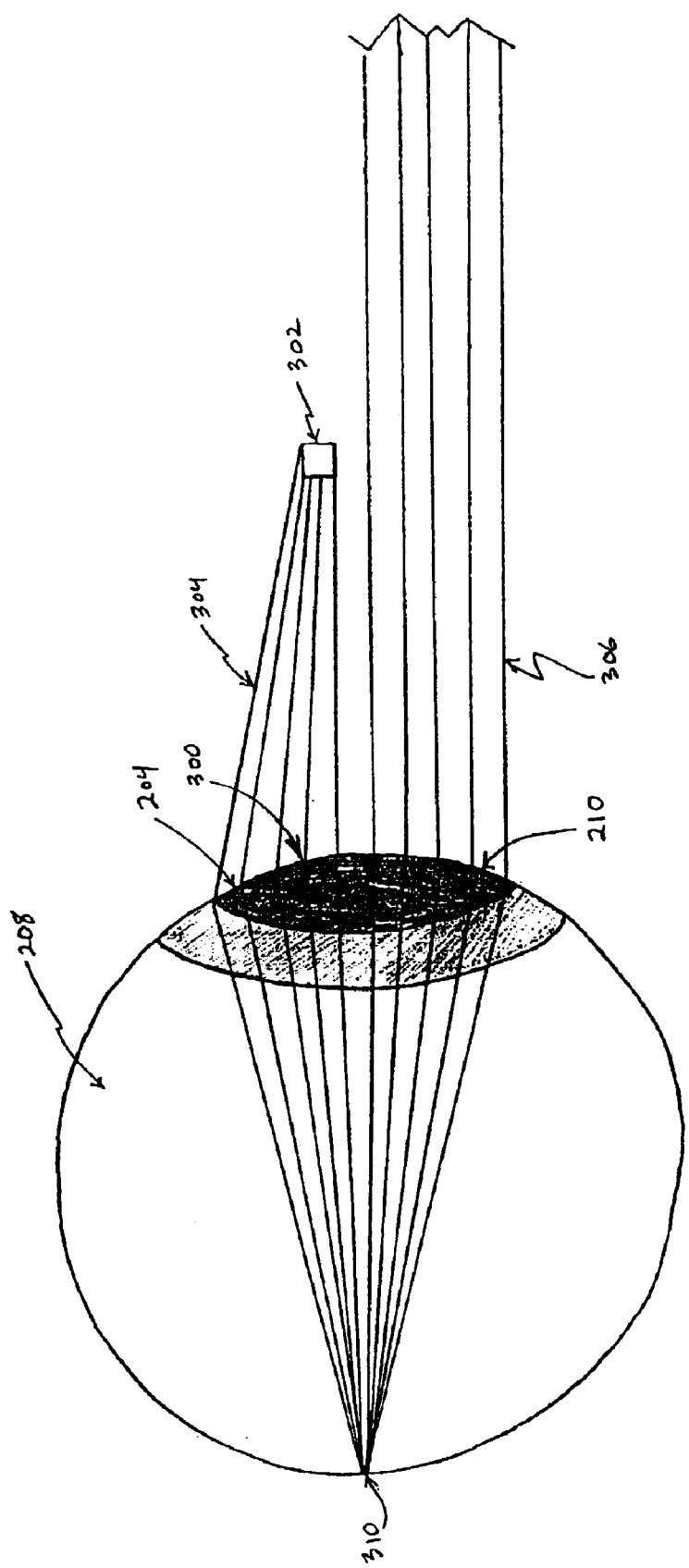
FIG. 3 is a cross-sectional side-view illustration of an eye, with rays of light reflected from both near and far objects penetrating the eye.

Referring now to FIG. 3, human eye 208 is generally configured to focus light, reflected from near objects 302 and far objects (not shown), to convene at a specific point (generally the fovea) on the optical part of the retina 310. The cornea 300 is generally configured to direct light rays to the lens of the eye (not shown), which focuses the light rays to land on the fovea. Light rays reflected from a far object 306 typically require different focusing than light rays 304 reflected from a near object 302. As discussed in reference to FIGS. 2a and 2b, superior area 204 of cornea 300 is typically used for vision of near objects 302 and inferior area 210 of cornea 300 is typically used for vision of far objects. Therefore, in accordance with one aspect of the present invention, superior area 204 of cornea may be treated to improve the ability of eye 208 to focus light reflected from near objects 302 and inferior eye may be treated to improve the ability of eye 208 to focus light reflected from far objects. In various embodiments, superior area 204 alone may be treated, inferior area 210 alone may be treated, both areas may be treated, and/or a transition zone between the two areas may be treated, the latter to create a smother focusing transition between superior area 104 and inferior area 210.

Figure 4A:
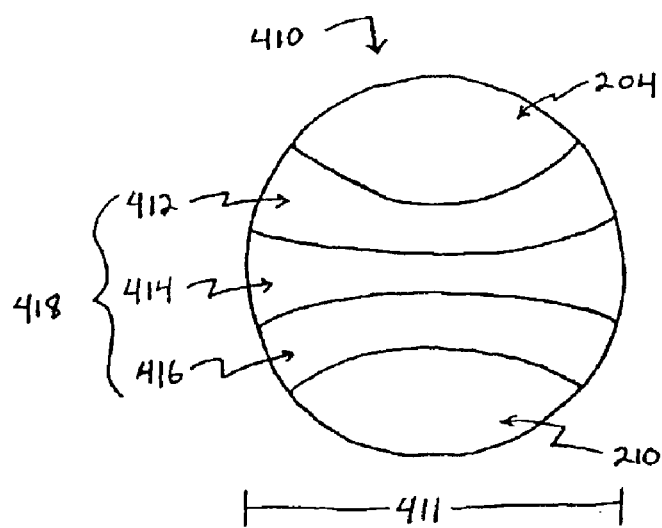
FIGS. 4a–c are front-view diagrams of diopter powers used to treat corneas in various embodiments of the present invention.

Referring now to FIG. 4a, according to one aspect of the present invention a "power map" may be drawn. Generally, a power map may include any plan, map, drawing, CAD design, model, and/or the like which may suitably be used for planning areas of treatment of a cornea. For example, power map 410 is a front-view map designating superior area 204, transition zone 418 and inferior area 210 of a cornea to be treated. Additionally, power map 410 includes three designated areas of transition zone, a superior transition zone 412, a middle transition zone 414 and an inferior transition zone 416. According to one aspect of the invention, superior zone 204, transition zone 418 and inferior zone 210 may be referred to generally as a treatment zone, which has a diameter 411. Typically, the treatment zone will correspond to an optical zone of a cornea, which is the portion of the cornea used for vision.

In an embodiment illustrated in FIG. 4a, power map 410 designates that a cornea will be treated to achieve a refraction of about −1 diopters (D) at superior area 204, −0.75D at superior transition zone 412, −0.50D at middle transition zone 414, −0.25D at inferior transition zone 416, and 0D at inferior area 210. Diameter 411 is between about 3 mm and about 7 mm, and more preferably between about 4 mm and about 6 mm.

Figure 4B:
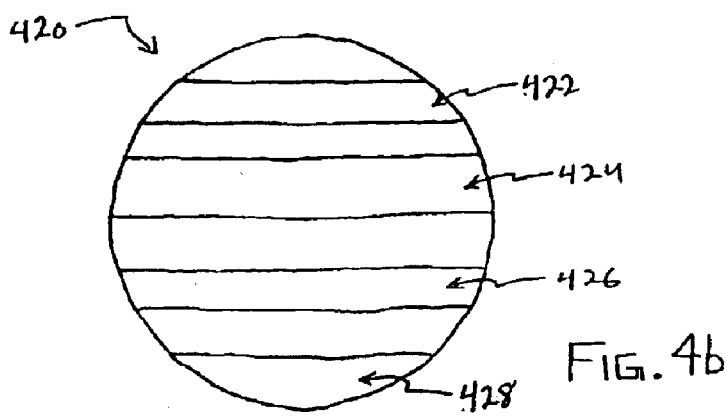

Referring now to FIG. 4b, a power map 420 alternatively includes treatment areas generally configured as horizontal strips, including a superior strip 422, a mid-superior strip 424, a mid-inferior strip 426 and inferior strip 428. In one embodiment, power map 420 may designate treatment such that superior strip 422 has a highest refractory power, mid-superior strip 424 has a moderate refractory power, mid-inferior strip 426 has a low refractory power and inferior strip 428 has no refractory power. In one embodiment, strips between the designated strips 422, 424, 426 and 428 are not treated. Alternatively, each in-between strip may be treated to have refractory powers between its two adjacent strips.

Figure 4C:
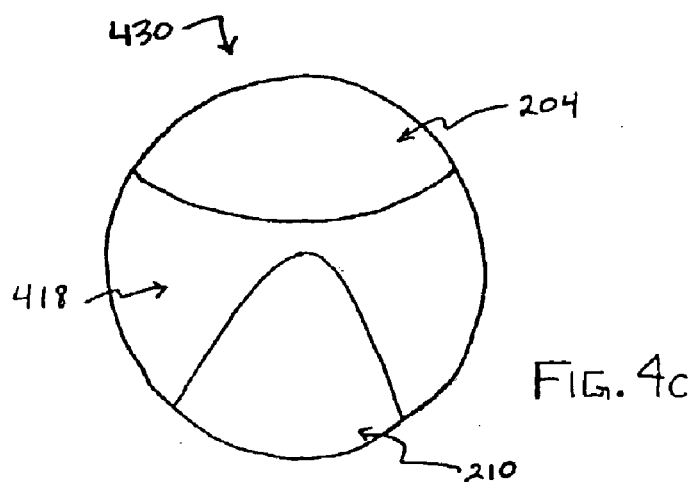

Referring now to FIG. 4c, an alternative power map 430 designates superior area 204, transition zone 418 and inferior area 210. In one embodiment, superior area 204 is treated to achieve a refraction of about −1D, inferior area 210 is treated to achieve 0D, and transition zone 418 is treated to achieve a gradual transition of refractory power between superior area 204 and inferior area 210.

Any suitable shape, configuration or combination of treatment areas, non-treated areas, refractory powers and the like is contemplated within the scope of the present invention. Additionally, a power map as contemplated in various embodiments may take any suitable form (or in some cases may not be used) to accomplish one or more objectives of the present invention. Therefore, the foregoing examples of various power maps are merely offered as examples of various ways in which treatment may be planned for a cornea. These examples should not limit the scope of the invention set forth in the appended claims.

According to another aspect of the invention, a of treatment zone (generally designated by power maps 410, 420, 430), which corresponds to an optical zone of a cornea, may be scaled to match a dimension of a pupil of an eye. For example, diameter 411 may be scaled to match a diameter of a pupil. In various embodiments, the scaling dimensions may be an area of the pupil, a diameter of the pupil, a radius, or the like. For example, the treatment zone may be decreased by about 20% from a diameter of about 5 mm to 4 mm for a patient with a 4 mm diameter pupil. In this case, superior area 204, inferior area 210 and transition zone 418 are each decreased by about 20%. In another example, a patient with a 5 mm diameter pupil may have a 2.5 mm diameter zone corrected for near-vision, while a patient with a 3 mm diameter pupil may have a 1.5 mm diameter zone corrected for near-vision. This scaling is desirable because it keeps the ratios of near, intermediate and far-vision nearly constant for varying pupil size.

According to one aspect of the present invention, a method for treating a cornea or an eye to correct presbyopia includes ablative photodecomposition of superior area 204 and inferior area 210. Superior area 204 is generally ablated to provide a near-distance refractive shape and inferior area 210 is generally ablated to provide a far-distance refractive shape. Optionally, transition zone 418 is also ablated. In various embodiments, a laser such as laser system 10 of FIG. 1 is used, but other suitable laser apparatus or systems may alternatively be used. Preferably, the invention employs a laser beam of smaller beam size than the total area of treatment zone.

While the above provides a full and complete disclosure of the preferred embodiments of the invention, various modifications, alternate constructions and equivalents may be employed as desired. Therefore, the above description should not be taken as limiting the scope of the invention which is defined by the appended claims.

What is claimed is:

1. An apparatus for use with a laser delivery system for treating presbyopia in a patient, the apparatus comprising a tangible medium having at least one machine readable code, the at least one machine readable code including instructions for a laser system to ablate a superior area of an optical zone of the patient's cornea to provide a near-distance vision upper refractive shape and an inferior area of the optical zone of the cornea to provide a far-distance vision lower refractive shape, wherein the superior area is disposed toward the top of the patient's head, when the patient is in a substantially vertical position, such that vision from the superior area is predominantly blocked by one or more parts of the patient's body and the inferior area is predominantly exposed when the eye focuses towards the horizon, and the inferior area is disposed below the superior area such that vision from the inferior area is predominantly blocked by one or more other parts of the patient's body and the superior area is predominantly exposed when the eye focuses in a downward direction.

2. An apparatus as in claim 1, wherein the at least one machine readable code further comprises instructions for the laser system to ablate a transition area of the optical zone of the cornea, the transition area being disposed between the superior area and the inferior area.

3. An apparatus as in claim 2, wherein the transition area is ablated to achieve a refraction of about −0.75 diopters in an area adjacent the superior area, a refraction of about −0.25 diopters in an area adjacent the inferior area, and a refraction of about −0.50 diopters in an area approximately midway between the superior area and the inferior area.

4. An apparatus as in claim 1, wherein the optical zone has a diameter of approximately 4–8 mm.

5. A system for treating a cornea of an eye to correct presbyopia, the cornea having an optical zone comprising a superior area primarily in an upper half of the optical zone and an inferior area primarily in a lower half of the optical zone the system comprising:

a laser delivery system being operable to deliver ablative radiation to the cornea; and a processor coupled to the laser delivery system to direct the laser delivery system to ablate the superior area of the optical zone to provide a near-distance vision upper refractive shape and the inferior area of the optical zone to provide a far-distance vision lower refractive shape, such that vision from the superior area is predominantly blocked by one or more parts of the patient's body and the inferior area is predominantly exposed when the eye focuses towards the horizon, and vision from the inferior area is predominantly blocked by one or more other parts of the patient's body and the superior area is predominantly exposed when the eye focuses in a downward direction.

6. A system as in claim 5, wherein the processor is further adapted to direct the laser delivery system to ablate a transition area of the optical zone, the transition area being disposed between the superior area and the inferior area.

7. A system as in claim 6, wherein the transition area is ablated to achieve a refraction of about −0.75 diopters in an area adjacent the superior area, a refraction of about −0.25 diopters in an area adjacent the inferior area, and a refraction of about −0.50 diopters in an area approximately midway between the superior area and the inferior area.

8. A system as in claim 5, wherein the optical zone has a diameter of approximately 4–8 mm.

9. A method for treating a cornea of an eye to correct presbyopia, the cornea having an optical zone comprising a superior area primarily in an upper half of the optical zone and an inferior area primarily in a lower half of the optical zone, the method comprising:

ablating the superior area of the optical zone to provide a near-distance vision upper refractive shape; and ablating the inferior area of the optical zone to provide a far-distance vision lower refractive shape.

10. The method as in claim 9, wherein the superior area is ablated to achieve a refraction of about −1 diopter and the inferior area is ablated to achieve a refraction of about 0 diopters.

11. A method as in claim 9, further comprising ablating a transition area of the optical zone, the transition area being disposed between the superior area and the inferior area.

12. A method as in claim 11, wherein the transition area is ablated to achieve a refraction of about −0.75 diopters in an area adjacent the superior area, a refraction of about −0.25 diopters in an area adjacent the inferior area, and a refraction of about −0.50 diopters in an area approximately midway between the superior area and the inferior area.

13. A method as in claim 9, wherein the optical zone has a diameter of approximately 4–8 mm.

14. A method as in claim 9, wherein vision from the superior area is predominantly blocked by one or more parts of the patient's body and the inferior area is predominantly exposed when the patient is in a substantial vertical position and when the eye focuses towards the horizon, and vision from the inferior area is predominantly blocked by one or more other parts of the patient's body and the superior area is predominantly exposed when the eye focuses in a downward direction.

15. A method for reprofiling a cornea of an eye from an initial shape to a multifocal aspheric shape for correcting presbyopia, the cornea having an optical zone comprising a superior area primarily in an upper half of the optical zone and an inferior area primarily in a lower half of the optical zone, the method comprising:

aligning a laser system with the eye, the laser system being operable to deliver ablative radiation to the cornea;

ablating the cornea to an ablated shape by selectively exposing the cornea to the ablative radiation so that the optical zone extends across the pupil, wherein the superior area is ablated to provide a near-distance vision upper refractive shape having a refraction of about −1 diopter and the inferior area is ablated to provide a far-distance vision lower refractive shape having a refraction of about 0 diopters; and covering the ablated surface to produce a final aspheric corneal surface.

16. A method as in claim 15, wherein the optical zone further comprises a transition area disposed between the superior and inferior areas.

17. A method as in claim 16, wherein the transition area is ablated to achieve a refraction of about −0.75 diopters in an area adjacent the superior area, a refraction of about −0.25 diopters in an area adjacent the inferior area, and a refraction of about −0.50 diopters in an area approximately midway between the superior area and the inferior area.

* * * * *